United States Patent [19]
Coates

[11] Patent Number: 5,246,928
[45] Date of Patent: Sep. 21, 1993

[54] THIADIAZINONES FOR STIMULATING CARDIAC ACTIVITY

[75] Inventor: William J. Coates, Welwyn Garden City, England

[73] Assignee: Smith Kline & French Laboratories Limited, Welwyn Garden City, England

[21] Appl. No.: 727,774

[22] Filed: Jul. 10, 1991

Related U.S. Application Data

[62] Division of Ser. No. 452,072, Dec. 18, 1989, Pat. No. 5,066,653, which is a division of Ser. No. 918,425, Oct. 14, 1986, Pat. No. 4,906,628.

[51] Int. Cl.⁵ .................. C07D 285/16; A61K 31/54
[52] U.S. Cl. ..................................... 514/222.5; 544/8
[58] Field of Search .......................... 544/8; 514/222.5

[56] References Cited

PUBLICATIONS

Afridi et al., Journal of the Chemical Society, Perkins Transactions I(1977) 1428–1436.

Primary Examiner—Mukund J. Shah
Assistant Examiner—Matthew V. Grumbling
Attorney, Agent, or Firm—Mary E. McCarthy; Stephen Venetianer; Edward T. Lentz

[57] ABSTRACT

This invention relates to N-phenylpyridone derivatives which have inotropic, vasodilator and bronchodilator activity. A compound of the invention is 5-methyl-6-[4-(4-oxo-1,4-dihydropyridin-1-yl)phenyl]-4,5-dihydro-3(2H)pyridazinone.

13 Claims, No Drawings

THIADIAZINONES FOR STIMULATING CARDIAC ACTIVITY

This is a divisional of application Ser. No. 07/452,072 filed Dec. 18, 1989, now U.S. Pat. No. 5,066,653 which is a divisional of application Ser. No. 06/918,425, filed Oct. 14, 1986, now U.S. Pat. No. 4,906,628 dated Mar. 6, 1990.

The present invention relates to pyridone derivatives and in particular to such compounds having a substituted phenyl group at the 1-position of the pyridone ring. This invention further relates to pharmaceutical compositions containing them and a method of stimulating cardiac activity by administering them. The compounds of this invention are selective phosphodiesterase type III inhibitors and are of use in combatting such conditions wherein such inhibition is thought to be beneficial. Thus the compounds of this invention are positive inotropic agents and vasodilators and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic reversible obstructive lung diseases such as asthma and bronchitis. The major utility of the compounds of this invention is in the treatment of congestive heart failure, for such treatment the compounds have a very desirable profile of activity.

Accordingly the present invention provides compounds of the formula (1):

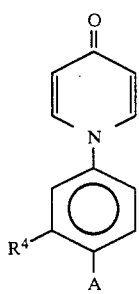

(1)

and pharmaceutically acceptable salts thereof, wherein A is a group of sub-formula (a), (b), (c) or (d):

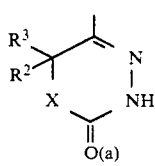

(a)

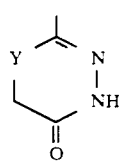

(b)

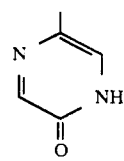

(c)

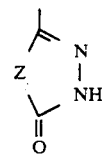

(d)

X is $CHR^1$, sulphur, oxygen or NH,
$R^1$ is hydrogen, or $R^1$ and $R^2$ together form a bond,
$R^2$ is hydrogen or methyl, or $R^1$ and $R^2$ together form a bond,
$R^3$ is hydrogen or together with $R^4$ form a methylene or 1,2-ethanediyl group,
Y is sulphur, oxygen or NH,
Z is sulphur or oxygen,
$R^4$ is hydrogen or together with $R^3$ form a methylene or 1,2-ethanediyl group,
with the proviso that X is $CHR^1$ or sulphur when $R^3$ together with $R^4$ form a methylene or 1,2-ethanediyl group.

Suitably A is a group of sub-formula (a) thus forming a pyridazin-3-one, dihydropyridazin-3-one, 1,3,4-thiadiazin-2-one, 1,3,4-oxadiazin-2-one, dihydro-1,2,4-triazin-3-one, dihydroindeno[1,2-c]pyridazin-3-one, indeno[1,2-c]pyridazin-3-one, tetrahydrobenzo[h]cinnolin-3-one, dihydrobenzo[h]cinnolin-3-one, dihydroindeno[1,2-e][1,3,4]thiadiazin-2-one or dihydronaphtho[1,2-e][1,3,4]thiadiazin-2-one ring system.

Suitably X is $CHR^1$, sulphur or NH, preferably X is $CHR^1$ or NH.

Particularly X is $CHR^1$.

Suitably when X is $CHR^1$, $R^1$ and $R^2$ together form a bond.

Preferably $R^2$ is methyl.

Suitably $R^3$ and $R^4$ together form a methylene group.

Preferably $R^3$ is hydrogen.

Suitably A is a group of sub-formula (b) thus forming a 1,3,4-thiadiazin-5-one, 1,3,4-oxadiazin-5-one or dihydro1,2,4-triazin-6-one ring system.

Suitably Y is sulphur or oxygen, preferably Y is sulphur.

Suitably A is a group of sub-formula (c) thus forming a pyrazin-2-one ring system.

Suitably A is a group of sub-formula (d) thus forming a 1,3,4-thiadiazol-2-one or 1,3,4-oxadiazol-2-one ring system.

Particular compounds of this invention are:
5-methyl-6-[4-(4-oxo-1,4-dihydropyridin-1-yl)phenyl]-4,5-dihydro-3(2H)-pyridazinone,
6-[4-(4-oxo-1,4-dihydropyridin-1-yl)phenyl]-4,5-dihydro-3(2H)-pyridazinone,
6-[4-(4-oxo-1,4-dihydropyridin-1-yl)phenyl]-3(2H)pyridazinone,
2-[4-(4-oxo-1,4-dihydropyridin-1-yl)phenyl]-4H,6H-1,3,4-thiadiazin-5-one, 2-[4-(4-oxo-1,4-dihydropyridin-1-yl)phenyl]-4H,6H-1,3,4-oxadiazin-5-one, 6-[4-(4-oxo-1,4-dihydropyridin-1-yl)phenyl]-4,5-dihydro-1,2,4-triazin-3(2H)-one, 6-[4-(4-oxo-1,4-dihydropyridin-1-yl)phenyl]-5-methyl-4,5-dihydro-1,2,4-triazin-3(2H)-one, 7-(4-oxo-1,4-dihydropyridin-1-yl)-9a-methyl-9,9a-dihydroindeno[1,2-e][1,3,4]thiadiazin-2(3H)-one, 7-(4-oxo-1,4-dihydropyridin-1-yl)-9,9a-dihydroindeno[1,2-e][1,3,4]thiadiazin-2(3H)-one, 5-[4-(4-oxo-1,4-dihydropyridin-1-yl)phenyl]-6-methyl-3H,6H-1,3,4-thiadiazin-2-one, 5-[4-(4-oxo-1,4-dihydropyridin-1-yl)phenyl]-2(1H)pyrazinone, 7-(4-oxo-1,4-dihydropyridin-1-yl)-[5H]indeno[1,2-c]pyridazin-3(2H)-one, 8-(4-oxo-1,4-dihydropyridin-1-yl)-4,4a,5,6-tetrahydrobenzo[h]cinnolin-3(2H)-one, 5-[4-(4-oxo-1,4-dihydropyridin-1-yl)phenyl]-1,3,4-thiadiazol-2(3H)-one, and 5-[4-(4-oxo-1,4-dihydropyridin-1-yl)phenyl]-1,3,4-oxadiazol-2(3H)-one, and pharmaceutically acceptable salts thereof.

This invention covers all tautomeric forms of compounds of formula (1). This invention also covers all optical isomers of the compounds of formula (1) in the resolved and racemic states in which $R^2$ is hydrogen and $R^3$ together with $R^4$ form a methylene or 1,2-ethanediyl group, or $R^2$ is methyl. In particular when $R^2$ is methyl and $R^1$, $R^3$ and $R^4$ are all hydrogen the (R) isomer of a compound of the formula (1) is preferred. When $R^2$ is methyl, $R^3$ and $R^4$ are both hydrogen and X is sulphur, oxygen or NH the (S) isomer of a compound of the formula (1) is preferred.

Compounds of the formula (1) may form pharmaceutically acceptable salts with acids such as hydrochloric, hydrobromic, sulphuric, phosphoric, methanesulphonic and ethanesulphonic acids.

Compounds of the formula (1) wherein X is $CHR^1$ and $R^1$ and $R^2$ together form a bond or A is a group of sub-formula (c) or (d) may form pharmaceutically acceptable salts with metal ions, such as alkali metals for example sodium and potassium, or alkaline earth metals for example calcium and magnesium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, parenterally, trans-dermally, rectally, via inhalation or via buccal administration.

Compounds of formula (1) and their pharmaceutically acceptable salts which are active when given orally or via buccal administration can be formulated as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 3 mg/Kg, and preferably from 0.005 mg/Kg to 1.5 mg/Kg, and each dosage unit for parenteral administration contains suitably from 0.001 mg/Kg to 1 mg/Kg, of a compound of formula (1) or a pharmaceutically acceptable salt thereof calculated as the free base.

The daily dosage regimen for oral administration is suitably about 0.001 mg/Kg to 12 mg/Kg, of a compound of formula (1) or a pharmaceutically acceptable salt thereof calculated as the free base. The daily dosage regimen for parenteral administration is suitably about 0.001 mg/Kg to 4 mg/Kg, for example about 0.005 mg/Kg to 1 mg/Kg, of a compound of the formula (1) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the invention are also bronchodilators and are useful in chronic reversible obstructive lung disease for example asthma and bronchitis. Such conditions can be treated by administration orally, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are vasodilators for example hydralazine, angiotensin converting enzyme inhibitors for example captopril, antianginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:

a) reacting a compound of the formula (2):

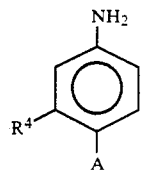

wherein $R^4$ and A are as hereinbefore defined, with 4H-pyran-4-one or a chemical equivalent thereof;

b) reacting a compound of the formula (3):

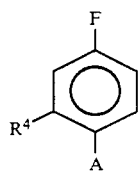

wherein $R^4$ and A are as hereinbefore defined, with 4-hydroxypyridine;

c) for compounds wherein X is $CHR^1$ and $R^1$ is as hereinbefore defined, reacting a compound of the formula (4):

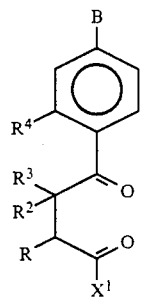

wherein $R^2$, $R^3$ and $R^4$ are as hereinbefore defined, B is

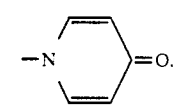

R is a group $R^1$ as hereinbefore defined or R can be OH when $R^2$ is hydrogen, and $X^1$ is a displaceable group, with hydrazine or a chemical equivalent thereof and when R is OH followed by dehydration:

d) for compounds wherein X is NH, reacting a compound of the formula (5):

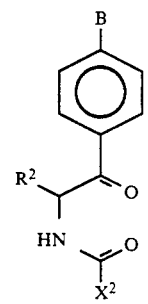

wherein $R^2$ is as hereinbefore defined, B is

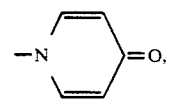

and $X^2$ is a leaving group, with hydrazine or a chemical equivalent thereof, e) for compounds wherein X is sulphur, reacting a compound of the formula (6):

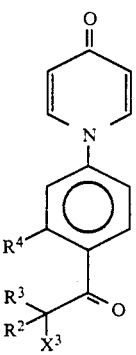

wherein $X^3$ is halo, $R^2$, $R^3$ and $R^4$ are as hereinbefore defined, provided that $R^2$ is hydrogen when $R^3$ together with $R^4$ forms a methylene or 1,2-ethanediyl group, with a compound of the formula (7):

wherein $R^5$ is $C_{1-6}$alkyl;

f) for compounds wherein X is sulphur, cyclising a compound of the formula (8):

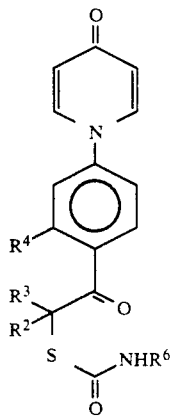

wherein $R^2$, $R^3$ and $R^4$ are as hereinbefore defined and $R^6$ is optionally protected amino, in the presence of acid, g) for compounds wherein X is oxygen, cyclising a compound of the formula (9):

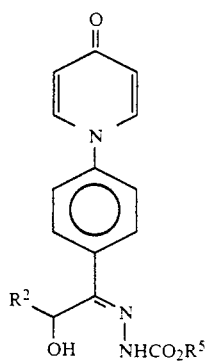

wherein $R^2$ and $R^5$ are as hereinbefore defined;

h) for compounds wherein Y is sulphur, treating a compound of the formula (10):

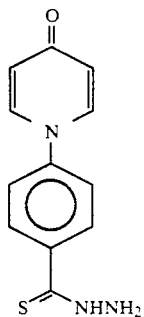

with a haloacetic acid;

i) for compounds wherein Y is oxygen, cyclising a compound of the formula (11):

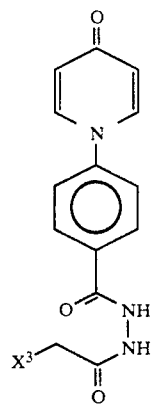

wherein $X^3$ is halo; or j) for compounds wherein Y is NH, treating a compound of the formula (12):

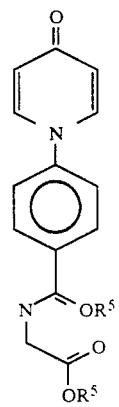

wherein $R^5$ is as hereinbefore defined, with hydrazine or a chemical equivalent thereof;

and thereafter optionally:

i) dehydrogenating a compound of the formula (1) wherein X is $CHR^1$, $R^1$ is hydrogen and $R^2$ is hydrogen to the corresponding compound wherein $R^1$ and $R^2$ together form a bond, ii) forming a pharmaceutically acceptable salt.

The reaction between a compound of the formula (2) and 4H-pyran-4-one or a chemical equivalent thereof is suitably performed at ambient or elevated temperature, for example 15°–190° C., preferably 30°–100° C. or at the reflux temperature of a suitable solvent. The reaction is conveniently performed in a solvent such as a $C_{1-4}$alkanol, for example ethanol or n-propanol, aqueous or glacial acetic acid, water or dimethylsulphoxide. Suitably the reaction is performed under acidic conditions, preferably the reaction is carried out in water acidified with hydrochloric acid or acetic acid.

By a chemical equivalent of 4H-pyran-4-one we mean a reagent which can be reacted with a primary amine to afford a N-substituted pyridin-4-one compound. Examples of chemical equivalents of 4H-pyran-4-one include chelidonic acid (13), 1,5-bis(dimethylamino)-1,4-pentadien-3-one (14) (Synth. Commun. 1983, 13, 1137) or 1,4-pentadiyn-3-one (15) (Ber. 1963, 96, 2504):

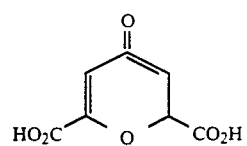
(13)

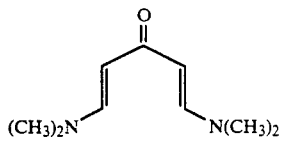
(14)

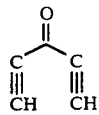
(15)

The reaction between a compound of formula (2) and chelidonic acid comprises two decarboxylation steps. Preferably the reaction is performed in a similar manner to that described by Katritzky et al., Journal Heterocyclic Chemistry 21, 1465-7, (1984), for example in dimethylsulphoxide at reflux.

The reaction between a compound of the formula (3) and 4-hydroxypyridine is conveniently performed at an elevated temperature, for example between 80° to 150° C. Suitably the reaction is performed in an aprotic solvent, such as dimethylformamide or N-methylpyrrolidin-2-one, in the presence of a base such as sodium hydride or potassium tert-butoxide.

The reaction between compounds of the formulae (4), (5) or (12) and hydrazine or a chemical equivalent thereof is suitably performed at ambient or elevated temperature, for example 15° C.-120° C., preferably about 30° C.-80° C. or at reflux temperature of a suitable solvent. The reaction is conveniently performed in a solvent such as water, a $C_{1-4}$alkanol for example methanol, ethanol or n-propanol, or aqueous or glacial acetic acid. Suitably in the compounds of the formula (4) $X^1$ is hydroxy, $C_{1-6}$alkoxy, amino or $C_{1-6}$alkylamino. When R is OH in the compounds of the formula (4) dehydration either occurs during the reaction or an additional step of dehydration (e.g. treatment with an acid e.g. hydrochloric acid in acetic acid) is carried out. Suitably in a compound of the formula (5) $X^2$ is $C_{1-6}$alkoxy. Suitably in a compound of the formula (12) $R^5$ is methyl or ethyl.

By a chemical equivalent of hydrazine we mean hydrazine hydrate, hydrazine ethanolate or a similar solvate. Preferably hydrazine is used in the form of hydrazine hydrate.

Suitably the reaction of the compounds of the formulae (6) and (7) is performed in an organic solvent for example a $C_{1-4}$alkanol such as ethanol, or in acetonitrile. The reaction is conveniently performed at an elevated temperature for example under reflux conditions. Suitably $X^3$ is bromo or chloro, preferably bromo. Suitably $R^5$ is methyl.

Suitably the cyclisation of a compound of the formula (8) is performed in an aqueous inorganic acid, for example hydrochloric acid, or in an organic solvent containing an aqueous inorganic acid, for example in a $C_{1-4}$alkanol, such as ethanol in admixture with hydrochloric acid. The cyclisation is conveniently performed at an elevated temperature for example 60° C. to 140° C., preferably at reflux temperature for convenience.

The cyclisation may be performed on a compound of the formula (8) wherein $R^6$ is amino, or a protected variant of the compound of the formula (8), for example protected on the hydrazine function by an acid-labile protecting group for example isopropylidene or benzylidene i.e. $R^6$ is $-N=C(CH_3)_2$ or $-N=CHC_6H_5$.

Suitably the cyclisation of a compound of the formula (9) is performed in the presence of a base, for example sodium ethoxide, in a solvent, for example ethanol, at ambient temperature.

A compound of the formula (10) is suitably treated with chloro- or bromoacetic acid in aqueous solution in the presence of a base, for example sodium hydroxide, at ambient temperature, followed by acidification of the reaction mixture with for example acetic acid.

In general the cyclisation of a compound of the formula (11) is performed in the presence of a base, for example sodium hydride, in a dipolar aprotic solvent such as dimethylformamide, or with an alkali metal carbonate such as potassium carbonate in acetone, at an elevated temperature for example under reflux conditions. Suitably $X^3$ in a compound of the formula (11) is bromo or chloro.

Methods of dehydrogenation of a compound of the formula (1) wherein X is $CHR^1$, and $R^1$ and $R^2$ are both hydrogen, include treatment with m-nitrobenzene sulphonic acid and base or with bromine in acetic acid.

The compounds of the formulae (2) and (3) wherein X is $CHR^1$, and $R^1$, $R^2$, $R^3$ and $R^4$ are as hereinbefore defined are known, or preparable in conventional manner, from Curran et al., J. Medicinal Chemistry, 17, p273, (1974) and European Patent Applications 0150937 and 0181145.

The compounds of the formulae (2) and (3) wherein X is oxygen, sulphur or NH, and $R^3$ and $R^4$ are both hydrogen, or Y is oxygen, sulphur or NH are known, or preparable in conventional manner from European Patent Applications 52442 and 123254.

The compounds of the formulae (2) and (3) wherein X is sulphur and $R^3$ together with $R^4$ is a methylene or 1,2-ethanediyl group are known, or preparable in conventional manner from European Patent Application 145236.

The compounds of the formulae (2) and (3) wherein A is a pyrazinone ring are known, or preparable in conventional manner from European Patent Application 96517.

The compounds of the formula (2) wherein Z is oxygen or sulphur can be prepared by reducing a compound of the formula (16):

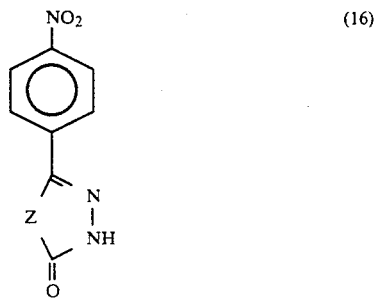
(16)

wherein Z is oxygen or sulphur.

Suitably when Z is sulphur the reduction is performed with sodium sulphide in a mixture of dioxane and water. Suitably when Z is oxygen the reduction is performed with hydrogen in the presence of palladium on carbon in a suitable solvent such as ethanol.

The compounds of the formulae (3) and (16) wherein Z is sulphur are known or preparable in conventional manner from Eur. J. Med. Chem.-Chim. Ther., 1985, 20, No. 1, 33-36.

The compounds of the formulae (3) and (16) wherein Z is oxygen are suitably prepared from a compound of the formula (17):

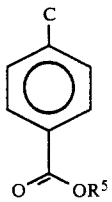
(17)

wherein C is fluoro or nitro and $R^5$ is $C_{1-6}$alkyl, by successive treatment with i) hydrazine or a chemical equivalent thereof, and ii) carbonyldiimidazole.

The (−) and (+) isomers of a compound of the formula (2) wherein $R^2$ is hydrogen and $R^3$ together with $R^4$ forms a methylene or 1,2-ethanediyl group, or $R^2$ is methyl can be separated by passage of racemic compound over a chiral phase chromatography column. The appropriate fractions are collected, rechromatographed as necessary, solvent is evaporated and the desired isomer isolated in conventional manner. The (−) and (+) isomers of a compound of the formula (2) wherein $R^2$ is methyl and $R^1$, $R^3$ and $R^4$ are all hydrogen are respectively the (R) and (S) isomers.

The resolved form of a compound of the formula (1) can be prepared by reaction of the corresponding resolved form of a compound of formula (2) with 4H-pyran-4-one or a chemical equivalent thereof.

The compounds of the formula (4) wherein B is

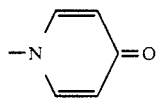

can be prepared by the following general routes:
a) by reaction of a compound of the formula (18):

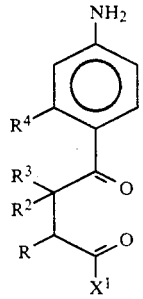
(18)

wherein R, $R^2$, $R^3$, $R^4$ and $X^1$ are as hereinbefore defined, with 4H-pyran-4-one or a chemical equivalent thereof in an analogous manner to that described for reacting a compound of the formula (2) with 4H-pyran-4-one or a chemical equivalent thereof; or
b) for compounds wherein $X^1$ is amino, hydroxy or $C_{1-6}$alkoxy, by reaction of a compound of the formula (4):

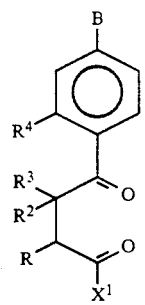
(4)

wherein B is fluoro, $X^1$ is amino, hydroxy or $C_{1-6}$alkoxy and R, $R^2$, $R^3$ and $R^4$ are as hereinbefore defined, with 4-hydroxypyridine. Suitably the reaction is performed at an elevated temperature, for example at about 80°-150° C., particularly at 100°-140° C. Suitably the reaction is performed in an aprotic solvent, such as dimethylformamide, preferably in N-methylpyrrolidin-2-one in the presence of a base such as sodium hydride or potassium tert-butoxide. Alternatively the reaction is performed in an aqueous $C_{1-4}$alkanol, for example n-butanol, in the presence of a base such as sodium hydroxide at an elevated temperature, for example under reflux conditions. Preferably when $X^1$ is hydroxy the reaction is performed in water in the presence of a base such as sodium hydroxide at an elevated temperature, for example under reflux conditions or in an autoclave at a temperature of about 140° C.

The compounds of the formula (4) wherein B is fluoro or

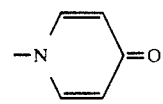

can be prepared by the following general routes:
a) for compounds wherein $X^1$ is hydroxy, R is hydroxy and $R^2$ is hydrogen, or R and $R^2$ together form a bond, by reaction of a compound of the formula (19):

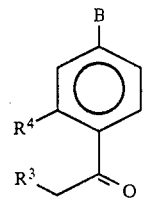
(19)

wherein B is fluoro or

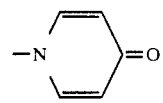

and $R^3$ and $R^4$ are as hereinbefore defined, with glyoxylic acid or a chemical equivalent thereof. By a chemical equivalent of glyoxylic acid we mean a solvate such as the hydrate or a combination of reagents which can generate glyoxylic acid in situ e.g. a mixture of tartaric acid and sodium metaperiodate. Preferably a compound of the formula (19) is fused with glyoxylic acid to afford a compound of the formula (4) which is dissolved in aqueous ammonia to pH 8 and reacted with hydrazine at an elevated temperature to give a compound of the formula (1) or (3) wherein X is $CHR^1$, $R^1$ and $R^2$ together form a bond, and $R^3$ and $R^4$ are as hereinbefore defined;

b) for compounds wherein $X^1$ is $C_{1-6}$alkoxy or hydroxy and R is hydrogen, by formation of the sodium derivative of a compound of the formula (20):

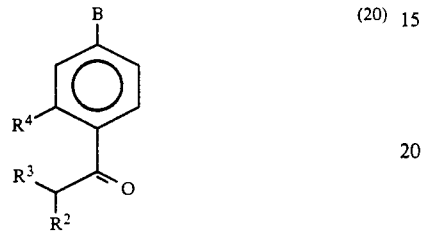
(20)

wherein B is fluoro or

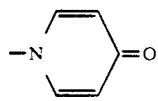

and $R^2$, $R^3$ and $R^4$ are as hereinbefore defined, and reaction with a $C_{1-6}$alkyl bromoacetate, followed by optional hydrolysis. Suitably the sodium derivative is formed by reaction with sodium hydride. Preferably the alkyl bromoacetate is ethyl bromoacetate. Suitably the hydrolysis is carried out under aqueous acidic conditions;

c) for compounds wherein $X^1$ is hydroxy or amino, R is hydrogen and $R^2$, $R^3$ and $R^4$ are as hereinbefore defined provided that $R^2$ is hydrogen when $R^3$ together with $R^4$ forms a methylene or 1,2-ethanediyl group, by reaction of a compound of formula (20) as hereinbefore defined provided that $R^2$ is hydrogen when $R^3$ together with $R^4$ forms a methylene or 1,2-ethanediyl group, with a Mannich reagent to give an intermediate of formula (21) in which $R^5$ is $C_{1-6}$alkyl, followed by optional quaternisation to give an intermediate of formula (22) in which $X^4$ is a halide or methylsulphate, treatment with potassium cyanide to give a nitrile of formula (23) and hydrolysis.

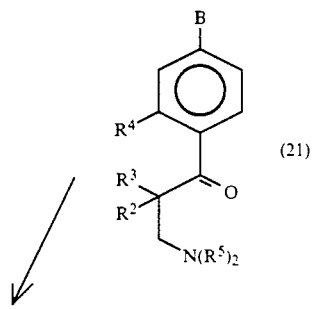
(21)

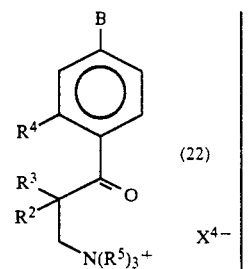
(22)

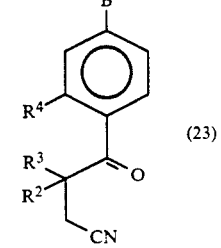
(23)

Examples of Mannich reagents are a mixture of dimethylamine and formaldehyde, and bis(dimethylamino)-methane. Preferably a slight excess of Mannich reagent is used, for example 1.3 molar equivalents. Preferably the reaction is carried out in the presence of an inert organic solvent for example $C_{1-4}$alkanols. Preferably the reaction is carried out at an elevated temperature, for example 60°–100° C., preferably at the reflux temperature of the reaction mixture.

Preferably quaternisation is carried out by reaction with an alkyl halide or a dialkyl sulphate.

Preferably the treatment with potassium cyanide is carried out in the presence of a solvent, for example water, $C_{1-4}$alkanols, acetic acid and aqueous mixtures thereof.

The acids (4) wherein $X^1$ is hydroxy can be prepared by hydrolysis of the nitriles (23), using aqueous acids or bases, carried out at elevated temperatures, e.g. 100° C.

The amides (4) wherein $X^1$ is amino are prepared by hydrolysis of the nitriles (23), using concentrated acids, preferably concentrated sulphuric acid, carried out at moderate temperatures;

d) for compounds wherein $X^1$ is hydroxy and R is hydrogen, by reaction of a compound of the formula (24) wherein B is fluoro or

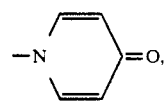

$R^2$, $R^3$ and $R^4$ are as hereinbefore defined and $X_5$ is a leaving group, with the sodium derivative of a dialkyl malonate (preferably diethylmalonate) to give a compound of the formula (25) wherein $R^5$ is $C_{1-6}$alkyl which is then hydrolysed and decarboxylated.

Suitably $X^5$ is chloro or bromo, preferably chloro.

Suitably the hydrolysis is carried out under aqueous acidic conditions, preferably when B is fluoro with a co-solvent such as dioxan.

(24) → (25)

The compounds of the formula (24) wherein $X^5$ is bromo can be prepared by bromination of a compound of the formula (20). Suitably the bromination is carried out using bromine or N-bromosuccinimide in a suitable solvent, preferably using bromine in acetic acid.

The compounds of the formula (24) wherein $X^5$ is chloro and $R^3$ and $R^4$ are both hydrogen can be prepared by acylation of fluorobenzene or N-phenylpyridin-4-one with an α-chloroacylchloride of formula (26):

(26)

wherein $R^2$ is hydrogen or methyl.

Suitably the acylation is carried out in the presence of a Lewis acid catalyst, such as aluminium trichloride. Suitably the acylation is carried out in a suitable solvent, such as dichloromethane or trichlorobenzene.

The compounds of the formula (20) wherein B is $$-N\diagup\diagdown=O$$

can be prepared by the following general routes:
a) by reaction of a compound of the formula (20) wherein B is fluoro with 4-hydroxypyridine. Suitably the reaction is performed at an elevated temperature, for example at about 80°–150° C. Suitably the reaction is performed in an aprotic solvent, such as dimethylformamide, or N-methylpyrrolidin-2-one in the presence of a base such as sodium hydride or potassium tert-butoxide, or
b) by reaction of a compound of the formula (27):

(27)

wherein $R^2$, $R^3$ and $R^4$ are as hereinbefore defined, with 4H-pyran-4-one or a chemical equivalent thereof in analogous manner to the reaction of a compound of the formula (2) with 4H-pyran-4-one or a chemical equivalent thereof.

Compounds of the formula (20) wherein B is fluoro and compounds of the formulae (18) and (27) are known, or preparable in conventional manner, from Curran et al., J. Medicinal Chemistry, 17, p273, (1974) and European Patent Applications 0150937 and 0181145.

A compound of the formula (5) wherein B is $$-N\diagup\diagdown=O$$

can be prepared by reacting a compound of the formula (5) wherein B is fluoro with 4-hydroxypyridine, in an analogous manner to that hereinbefore described for the reaction of a compound of the formula (4) wherein B is fluoro with 4-hydroxypyridine.

A compound of the formula (5) wherein B is $$-N\diagup\diagdown=O$$

or fluoro can be prepared from a compound of the formula (24) wherein B, $R^2$ and $X^5$ are as hereinbefore defined and $R^3$ and $R^4$ are both hydrogen, in a similar manner to that described in EP-52442, for example by reaction with sodium azide, followed by reduction of an azido intermediate to form an amino compound which is reacted with an alkyl chloroformate.

A compound of the formula (8) can be prepared by reacting a compound of the formula (24) wherein B is $$-N\diagup\diagdown=O$$

with a compound of the formula (28):

$$M^+\,{}^-OCSNHR^6 \qquad (28)$$

wherein $R^6$ is as hereinbefore defined and $M^+$ is a counter-ion, for example an alkali metal ion such as potassium or sodium or is an ammonium ion, in a similar manner to that described in EP-52442 and EP-A-145236.

A compound of the formula (6) (which is a compound of the formula (24) wherein B is $$-N\diagup\diagdown=O.$$

$X^5$ is halo and $R^2$, $R^3$ and $R^4$ are as hereinbefore defined provided that $R^2$ is hydrogen when $R^3$ together with $R^4$ forms a methylene or a 1,2-ethanediyl group) can be prepared as hereinbefore described for a compound of the formula (24).

A compound of the formula (9) can be prepared from a compound of the formula (24) wherein B is

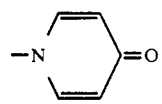

and $R^3$ and $R^4$ are both hydrogen in a similar manner to that described in EP-52442, for example by reaction with potassium acetate in acetic acid to afford an acetoxy compound which is hydrolysed by treatment with aqueous hydrochloric acid and is then reacted with an alkyl carbazate.

A compound of the formula (10) can be prepared from 4-(4-oxo-1,4-dihydropyridin-1-yl)benzaldehyde in a similar manner to that described in EP-52442, for example by successive treatment with i) sulphur and piperidine, ii) bromoacetic acid, iii) hydrogen sulphide and iv) hydrazine or a chemical equivalent thereof. 4-(4-Oxo-1,4-dihydropyridin-1-yl)benzaldehyde can be prepared by reacting 4-fluorobenzaldehyde with 4-hydroxypyridine.

A compound of the formula (11) can be prepared from ethyl 4-fluorobenzoate in a similar manner to that described in U.S. Pat. No. 4,508,718 and EP-52442, for example by successive treatment with i) 4-hydroxypyridine in the presence of a base such as sodium hydride, ii) hydrazine or a chemical equivalent thereof and iii) a haloacetylhalide such as chloroacetylchloride in the presence of a base such as potassium carbonate or triethylamine.

A compound of the formula (12) can be prepared in a similar manner to that described in EP-52442, for example from 4-(4-oxo-1,4-dihydropyridin-1-yl)benzoyl chloride by successive treatment with i) an alkyl glycinate and ii) an oxonium tetrafluoroborate of the formula $(R^5)_3OBF_4$ wherein $R^5$ is $C_{1-6}$alkyl. Suitably the 4-substituted benzoyl chloride is prepared by treating 4-aminobenzoic acid with 4H-pyran-4-one or a chemical equivalent thereof to afford 4-(4-oxo-1,4-dihydropyridin-1-yl)benzoic acid which is treated with thionyl chloride.

Pharmaceutically acceptable acid addition salts of the compounds of the formula (1) may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test methods, data, Description and Examples serve to illustrate this invention.

Cardiac Stimulant Activity-In vivo (Anaesthetised Cats)

In anaesthetised cats pretreated with a ganglion blocker (mecamylamine or pempidine) and propranolol, the compounds of the Examples cause increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative Duration# |
|---|---|---|
| 1 | 0.04 | *** |
| 2 | 0.40 | * |
| 3 | 0.47 | * |
| 4 | 0.06 | * |
| 5 | 0.22 | *** |
| 6 | 0.23 | * |
| 7 | 0.11 | *** |
| 8 | 0.07 | * |
| 9 | 0.05 | * |
| 10 | 0.07 | * |
| 13 | 0.78 | * |
| 14 | 0.82 | * |
| Amrinone | 5.6 | * |

Relative duration was estimated in the anaesthestized cats following the i.v. administration:
***long:
*short Minimal changes in blood pressure or heart rate were observed.

Cardiac Stimulant Activity-In vivo (Conscious Dogs)

The compound of Example 1 increased left ventricular dp/dt max in conscious dogs after intravenous administration at doses below 0.02 mg/kg. Oral administration caused positive inotropic responses at doses of 0.05 mg/kg and below. These positive inotropic responses persisted for more than 3 hours (maximum duration of measurement) without changes in blood pressure or heart rate. Therefore this compound is particularly beneficial with regard to 'force-rate' selectivity. In contrast amrinone is less active and is of shorter duration.

Inhibition of Phosphodiesterases

Three peaks of cyclic nucleotide phosphodiesterase activity [PDE (Peak I), PDE (Peak II) and PDE (Peak III)] from cat heart were separated by chromatography on DEAE Sepharose CL-6B (Diethylaminoethyl Cellulose with a bead size of 45-165 microns). Sepharose is a registered trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a 15×1.5 cm column of DEAE-Sepharose equilibrated with the homogenisation buffer. The PDE activities were eluted with a gradient of 0.05-1M Na acetate in 20 mM PIPES. There were three major peaks which had the following characteristics:

| PDE (Peak I) - eluted at 0.15 M Na acetate | | | |
|---|---|---|---|
| Substrate | 50 µg/ml calmodulin (+ = added) | Km (µM) | Relative $V_{max}$ |
| cyclic AMP | — | 0.5 | 1 |
| cyclic GMP | — | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
|---|---|---|
| Substrate | Km (µM) | Relative $V_{max}$ |
| cyclic AMP | 6 | 1 |
| cyclic GMP | 28 | 0.2 |

| PDE (Peak III) - eluted at 0.5 M Na acetate | | |
|---|---|---|
| Substrate | Km (μM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP though the preferred substrate is cyclic AMP. This activity is also insensitive to $Ca^{2+}$/calmodulin activation.

Enzyme assay

The enzyme was assayed by incubation at 37° for 4-30 min in 50 mM Tris, 5 mM $MgCl_2$, pH 7.5 with [3-H] cyclic nucleotide ($4 \times 10^5$ disintegrations $min^{-1}$) and [14-C] nucleotide 5' monophosphate ($3 \times 10^3$ disintegrations $min^{-1}$). The assay was stopped by boiling, and the [3-H] 5'monophosphate product separated from substrate on boronate columns (Davis, C. W. and Daly, J. W. (1979) J. Cyclic Nucleotide Res., 5, 65–74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25M acetic acid. The recovery of product as judged by [14-C] recovery was approximately 80%. All assays were linear with time of incubation and concentration of enzyme over the range used in these experiments.

Calculation of $IC_{50}$ values $IC_{50}$ values (the concentration of inhibitor required for 50% inhibition of activity) were obtained for PDE (Peak III) by incubation of the enzyme at 1 μM cyclic AMP, and a range of inhibitor concentrations from $0.1 \times IC_{50}$ to $100 \times IC_{50}$.

| Compound of Example | $IC_{50} \times 10^{-6}$ |
|---|---|
| 1 | 0.41 |
| 2 | 5.09 |
| 3 | 3.99 |
| 4 | 1.59 |
| 5 | 4.33 |
| 6 | 1.75 |
| 7 | 0.54 |
| 8 | 1.32 |
| 9 | 1.25 |
| 10 | 0.44 |
| 11 | 2.64 |
| 13 | 6.60 |
| 14 | 2.26 |
| 16 | 0.23 |
| 17 | 2.58 |
| Amrinone | 51.8 |
| Milrinone | 2.2 |

Specificity

The compounds described in the Examples showed no inhibition at up to $10^{-4}$M when incubated with PDE (Peak I) and either no or weak inhibition with respect to PDE (Peak II) i.e. they were selective PDE (Peak III) inhibitors. This specificity is an indication that the compounds are likely to have a force/rate selectivity in their cardiac stimulant activity with a low potential for inducing arrythmias.

Vasodilator Activity

The compounds of the Examples were tested in autoperfused anaesthetised cat hindquarters (autoperfused at constant blood flow). The i.v. dose to decrease hindquarters perfusion pressure (vasodilatation) by 15% is given as $ED_{15}$.

| Compound of Example | $ED_{50}$ (μm/kg) |
|---|---|
| 1 | 0.05 |
| 2 | 0.38 |
| 3 | 0.64 |
| 7 | 0.15 |
| 8 | 0.04 |

Bronchodilatation—In vivo

Male guinea-pigs of the Dunkin Hartley strain (530 g±6 g) were anaesthetised with Sagatal (pentobarbital sodium) (90 mg/kg i.p.). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., 195: pp 71–74, (1940)). A dose of histamine which gave approximately 150% increase in airway resistance was selected for i.v. administration. Bolus doses of the compound of Example 1 were administered (i.v.) one minute before the histamine challenge.

The compound of Example 1 reduced the histamine-induced bronchoconstriction. The threshold dose for this compound was $1 \times 10^{-8}$ mol/kg. The dose of the compound of Example 1 which reduced the histamine bronchoconstriction by 50% ($ED_{50}$) was $1.8 \times 10^{-6}$ mol/kg, demonstrating in-vivo anti-bronchoconstrictor activity.

Platelet Aggregation Inhibition—In vitro

Platelet rich plasma (PRP) was prepared from whole human blood anti-coagulated with 1/10 volume acid citrate dextrose. The citrated blood was centrifuged at 700 g for 5 minutes and the PRP removed. The remaining red cells and plasma were centrifuged for a further 15 minutes at 900 g and the platelet poor plasma removed. This was then mixed with the PRP to give a final platelet count of $2-3 \times 10^8$ cells/ml.

PRP was divided into 0.5 ml aliquots which were preincubated for 2 minutes to 37° C. before being placed in the sample chamber of an HG aggregometer connected to a Teckman chart recorder.

Aspirin was added to a concentration of 100 μM.

Aggregation to the endoperoxide mimetic U44069 (9,11-epoxymethano-$PGH_2$) was then examined in the absence and presence of a range of concentrations of the compound of Example 1.

The compound of Example 1 inhibited aggregation induced by the endoperoxide mimetic U44069 (10 μM) in aspirin-treated platelet rich plasma with an $IC_{50}$ value of 0.08±0.01 μM.

Description 1

(+) and (−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (2.0 g) dissolved in a mixture of acetonitrile (80 ml) and dichloromethane (30 ml) was added to a column of ionically bound (R)-N-(3,5-dinitrobenzoylphenyl)glycine on 40 μm λ-aminopropyl silanized silica (2.1 kg), packed at 1104 kPa (160 p.s.i.) (by slurrying with dichloromethane (1.5 L)) in a Jobin-Yvon medium pressure liquid chromatography system. The column was eluted with dichloromethane/methanol (199:1) over 9 hours at a rate of 80 ml min$^{-1}$. Detection was by u.v. at 280 nm. A broad peak was obtained from which fractions were collected. The earlier fractions were enriched (−) enantiomer. These fractions were combined and re-chromatographed through the same column with the same eluant.

The selected column fractions were evaporated, triturated with diethyl ether, filtered and the resultant solid washed with diethyl ether and dried at 80° C. for 18 hours to give (−)-6-(4-aminophenyl)-5-methyl-4,5-dihydro-3(2H)-pyridazinone, in approximately 100% enantiomeric excess, m.p. 203°-4° C.; $[\alpha]_D^{25} = -399°$ [concentration 0.74% in ethanol:water:conc. HCl (17:2:1)].

A sample of the (−) isomer was reacted with 3-bromopropionyl chloride to afford enantiomerically pure (−)-6-[4-(3-bromopropionamido)phenyl]-5-methyl-4,5-dihydro-3(2H)-pyridazinone, the absolute configuration of which was shown by a X-ray diffraction study to be (R).

The later fractions from the first column were enriched (+) enantiomer (approximately 75% enrichment) which was subjected to medium pressure liquid chromatography (Jobin-Yvon system) over a column of ionically bound (S)-N-(3,5-dinitrobenzoyl)phenylglycine on 25-40 μm λ-aminopropyl silanized silica (55 g) eluting with dichloromethane/methanol (199:1). The appropriate fractions were combined with fractions from another run and re-chromatographed through the same column.

The selected column fractions were evaporated, triturated with diethyl ether, filtered and the resultant solid washed with diethyl ether and dried at 80° C. for 18 hours to give (+)-6-(4-aminophenyl)-5-methyl-4,5-dihydro-3(2H)-pyridazinone, in approximately 100% enantiomeric excess, m.p. 206°-8° C.; $[\alpha]_D^{25} = +376°$ [concentration 0.74% in ethanol:water:conc. HCl (17:2:1)].

EXAMPLE 1

5-Methyl-6-[4-(4-oxo-1,4-dihydropyridin-1-yl)phenyl]-4,5-dihydro-3(2H)-pyridazinone A stirred mixture of 6-(4-aminophenyl)-5-methyl-4,5-dihydro-3(2H)-pyridazinone (1.0 g), 4H-pyran-4-one (0.52 g), water (20 ml), and concentrated hydrochloric acid (0.41 ml) was heated under reflux for 3½ hours. The resultant solid was dissolved in the minimum of hot water and the solution was neutralised with aqueous ammonia to give the crude product, 1.16 g, m.p. 249°-256° C. The product was recrystallised first from water to which a little 2N NaOH was added, and then from water alone to give the pure title compound, 0.82 g, m.p. 254°-256° C. (after melting and resolidifying at about 150° C.).

EXAMPLE 2

6-[4-(4-Oxo-1,4-dihydropyridin-1-yl)phenyl]-4,5-dihydro-3(2H)-pyridazinone

A stirred mixture of 6-(4-aminophenyl)-4,5-dihydro-3(2H)-pyridazinone hydrochloride (1.5 g), 4H-pyran-4-one (0.7 g), and water (20 ml), was heated under reflux for 4½ hours. The resultant solid was dissolved in the minimum of hot water and the solution was neutralised with ammonia to give the crude product. Recrystallisation from water gave the title compound, 0.73 g, m.p. 270°-272° C.

EXAMPLE 3

6-[4-(4-Oxo-1,4-dihydropyridin-1-yl)phenyl]-3(2H)-pyridazinone

A stirred mixture of 6-(4-aminophenyl)-3(2H)-pyridazinone hydrochloride (1.5 g), 4H-pyran-4-one (0.71 g), and water (20 ml), was heated under reflux for 2 hours. The pH of the hot solution was adjusted to 8 with aqueous ammonia and the mixture was cooled to give the crude product, 1.84 g, m.p. 338°-340° C. Recrystallisation from aqueous ethanol gave the title compound, 1.4 g, m.p. 339°-341° C.

EXAMPLE 4

2-[4-(4-Oxo-1,4-dihydropyridin-1-yl)phenyl]-4H,6H-1,3,4-thiadiazin-5-one

A stirred mixture of 2-(4-aminophenyl)-4H,6H-1,3,4-thiadiazin-5-one (1.0 g), 4H-pyran-4-one (0.51 g), water (20 ml) and concentrated hydrochloric acid (0.42 ml), was heated under reflux for 3 hours. The warm solution was neutralised with concentrated aqueous ammonia and cooled to give a solid, 1.33 g. Recrystallisation from methanol gave the title compound, 0.89 g, m.p. 289°-291° C.

EXAMPLE 5

2-[4-(4-Oxo-1,4-dihydropyridin-1-yl)phenyl]-4H,6H-1,3,4-oxadiazin-5-one

In a similar manner to that of Example 4, 2-(4-aminophenyl)-4H,6H-1,3,4-oxadiazin-5-one (1.4 g), gave a crude product which was recrystallised from ethanol to give the title compound, 0.48 g, m.p. decomposed >290° C.

EXAMPLE 6

6-[4-(4-Oxo-1,4-dihydropyridin-1-yl)phenyl]-4,5-dihydro-1,2,4-triazin-3(2H)-one

In a similar manner to that of Example 4, but under a nitrogen atmosphere, 6-(4-aminophenyl)-4,5-dihydro-1,2,4-triazin-3(2H)-one (0.7 g) gave a solid, 0.95 g, m.p. 285°-290° C. (dec). Recrystallisation from aqueous ethanol gave the title compound, 0.67 g, m.p. 334°-335° C. (dec).

EXAMPLE 7

6-[4-(4-Oxo-1,4-dihydropyridin-1-yl)phenyl]-5-methyl-4,5-dihydro-1,2,4-triazin-3(2H)-one In a similar manner to that of Example 6, 6-(4-aminophenyl)-5-methyl-4,5-dihydro-1,2,4-triazin-3(2H)-one (0.7 g), gave a solid (0.83 g), m.p. 314°-317° C. (dec).

Recrystallisation from aqueous ethanol gave the title compound, 0.57 g, m.p. 330°–331° C. (dec).

EXAMPLE 8

7-(4-Oxo-1,4-dihydropyridin-1-yl)-9a-methyl-9,9a-dihydroindeno[1,2-e][1,3,4]thiadiazin-2(3H)-one A stirred mixture of 7-amino-9a-methyl-9,9a-dihydroindeno[1,2-e][1,3,4]thiadiazin-2(3H)-one hydrochloride (1.4 g), 4H-pyran-4-one (0.55 g) and water (20 ml) was heated under reflux for 5½ hours. A partial solution of the crude solid in hot water was neutralised with aqueous ammonia, and the resultant solid was recrystallised twice from aqueous dimethylformamide to give the title compound 0.45 g, m.p. decomposed >250° C.

EXAMPLE 9

7-(4-Oxo-1,4-dihydropyridin-1-yl)-9,9a-dihydroindeno[1,2-e][1,3,4]thiadiazin-2(3H)-one In a manner similar to that of Example 8, 7-amino-9,9a-dihydroindeno[1,2-e][1,3,4]thiadiazin-2(3H)-one hydrochloride (1.0 g) gave a solid, 0.87 g, which was recrystallised from aqueous acetic acid to give the title compound, 0.38 g, m.p. decomposed >245° C.

EXAMPLE 10

5-[4-(4-Oxo-1,4-dihydropyridin-1-yl)phenyl]-6-methyl-3H,6H-1,3,4-thiadiazin-2-one A stirred mixture of 5-(4-aminophenyl)-6-methyl-3H,6H-1,3,4-thiadiazine-2-one (0.54 g), 4H-pyran-4-one (0.26 g), glacial acetic acid (0.15 g) and water (20 ml) was heated under reflux for 24 hours to give a solid, 0.54 g. Recrystallisation from aqueous ethanol gave the title compound, 0.28 g, which darkened at 265° C. and sublimed at 273°–275° C.

EXAMPLE 11

5-[4-(4-Oxo-1,4-dihydropyridin-1-yl)phenyl]-2(1H)-pyrazinone

A stirred mixture of 5-(4-aminophenyl)-2(1H)pyrazinone hydrochloride (1.5 g, from hydrolysis of the corresponding acetamido derivative with hydrochloric acid), 4H-pyran-4-one (0.71 g) and water (15 ml) was heated under reflux for 2½ hours under a nitrogen atmosphere. The resultant solution was neutralised to give a solid, 1.79 g, m.p. 345° C. (dec). Recrystallisation from aqueous ethanol gave the title compound, 0.93 g, m.p. 354°–357° C. (dec).

EXAMPLE 12

7-(4-Oxo-1,4-dihydropyridin-1-yl)-[5H]indeno[1,2-c]pyridazin-3(2H)-one

A stirred mixture of 7-amino-[5H]indeno[1,2-c]pyridazin-3(2H)-one hydrochloride (1.0 g) and 4H-pyran-4-one (0.48 g) in water (10 ml) was heated under reflux for 1 hour in a nitrogen atmosphere. The warm mixture was neutralised with aqueous ammonia to give a solid, 0.9 g, m.p. >300° C. This solid was triturated with warm dilute hydrochloric acid and washed with water to give the title compound, 0.42 g, m.p. >300° C.

EXAMPLE 13

8-(4-Oxo-1,4-dihydropyridin-1-yl)-4,4a,5,6-tetrahydrobenzo[h]cinnolin-3(2H)-one

A stirred mixture of 8-amino-4,4a,5,6-tetrahydrobenzo[h]cinnolin-3(2H)-one hydrochloride (1.5 g) and 4H-pyran-4-one (0.84 g) in water (40 ml) was heated under reflux for 2 hours in a nitrogen atmosphere. The resultant solid was washed with dilute hydrochloric acid to give a crude product, 0.5 g. Purification by column chromatography (silica gel, 9:1 chloroform: methanol) gave the title compound 0.18 g, m.p. >300° C.

EXAMPLE 14

5-[4-(4-Oxo-1,4-dihydropyridin-1-yl)phenyl]-1,3,4-thiadiazol-2(3H)-one i) A solution of 5-(4-nitrophenyl)-1,3,4-thiadiazol-2(3H)-one (2.82 g) and sodium sulphide (2.53 g) in dioxane (20 ml) and water (20 ml) was stirred at 85° C. for 2½ hours. The pH of the cooled reaction mixture was adjusted to 14 with aqueous sodium hydroxide (2N) and the resultant solution was extracted with dichloromethane (3×20 ml). The aqueous phase was neutralised with dilute hydrochloric acid and the resultant pale yellow solid was recrystallised from aqueous hydrochloric acid to afford 5-(4-aminophenyl)-1,3,4-thiadiazol-2(3H)-one hydrochloride, 1.65 g, m.p. >250° C.

ii) A mixture of 5-(4-aminophenyl)-1,3,4-thiadiazol-2(3H)-one hydrochloride (1.25 g), 4H-pyran-4-one (0.58 g), ethanol (10 ml) and water (50 ml) was stirred under reflux under nitrogen for 3½ hours. The cooled reaction mixture was filtered and the collected orange solid was washed with aqueous potassium hydrogen carbonate and water and was dried. The crude product (1.35 g) was treated with boiling dimethylformamide (200 ml) and the resultant suspension was cooled and filtered. The collected solid was washed with ethanol and ether, dried and suspended in water (100 ml). Sufficient aqueous sodium hydroxide (2N) was added to the suspension to form a solution which was filtered. The filtrate was acidified to pH 6 with hydrochloric acid which caused the precipitation of the title compound as a yellow solid, 0.96 g, m.p. 343°–4° C. (decomp).

EXAMPLE 15

5-[4-(4-Oxo-1,4-dihydropyridin-1-yl)phenyl]-1,3,4-oxadiazol-2(3H)-one i) A solution of methyl 4-nitrobenzoate (20 g) and hydrazine hydrate (11 g) in ethanol (200 ml) was stirred under reflux for 5 hours to afford 4-nitrobenzoyl hydrazide 16.8 g, m.p. 217°–219° C.

ii) A solution of carbonyldiimidazole (2.87 g) and 4-nitrobenzoyl hydrazide (1.32 g) in dimethylformamide (30 ml) was stirred at 100° C. for one hour. The solvent was removed by evaporation and the resultant solid was recrystallised from ethanol to afford 5-(4-nitrophenyl)1,3,4-oxadiazol-2(3H)-one, 0.75 g, m.p. 251°–252° C.

iii) 5-(4-nitrophenyl)-1,3,4-oxadiazol-2(3H)-one, (0.65 g) in ethanol (100 ml) was hydrogenated at 276 kPa (40 p.s.i.) in the presence of palladium on carbon at room temperature for one hour. The reaction mixture was filtered, the filtrate was evaporated to dryness and the resultant yellow solid was recrystallised from ethanol to afford (5-(4-aminophenyl)-1,3,4-oxadiazol-2(3H)-one, 0.46 g, m.p. 172°–173° C.

iv) A mixture of 5-(4-aminophenyl)-1,3,4-oxadiazol-2(3H)-one (0.41 g), 4H-pyran-4-one (0.24 g), and hydrochloric acid (2N, 1.15 ml) in water (25 ml) was stirred under reflux for 3 hours to afford a yellow solid. This solid was added to hot water with stirring and the resulting suspension was made alkaline (pH 8) with aqueous ammonia and was then filtered. The collected solid was dissolved in aqueous potassium carbonate and the resulting solution was neutralised with dilute acetic acid to afford an emulsion from which after centrifugation was obtained the title compound, 0.47 g, m.p. 220° C. (decomp), contaminated with potassium acetate.

EXAMPLE 16

(R)-5-Methyl-6-[4-(4-oxo-1,4-dihydropyridin-1-yl)phenyl]-4,5-dihydro-3(2H)-pyridazinone A mixture of (R)-6-(4-aminophenyl)-5-methyl-4,5-dihydro-3(2H)-pyridazinone (100 mg), 4H-pyran-4-one (52 mg) and hydrochloric acid (0.1N, 1 ml) in water (1.3 ml) was stirred under reflux under nitrogen for 3 hours. Aqueous ammonia (880, 0.01 ml) was added to the cooled reaction mixture to afford the title compound which was collected, washed with water and dried, 91 mg, m.p. 257°–8° C. (softens 120° C.), $[\alpha]_D^{25} = -369.5°$ (1.07% in dimethylformamide).

EXAMPLE 17

(S)-5-Methyl-6-[4-(4-oxo-1,4-dihydropyridin-1-yl)phenyl]-4,5-dihydro-3(2H)-pyridazinone A mixture of (S)-6-(4-aminophenyl)-5-methyl-4,5-dihydro-3(2H)-pyridazinone (147 mg), 4H-pyran-4-one (78 mg) and hydrochloric acid (0.1N, 1.5 ml) in water (2 ml) was stirred under reflux under nitrogen for 3 hours. The reaction mixture was cooled to afford the title compound, which was collected, washed with water and dried, 110 mg, m.p. 256°–7° C. (softens 80° C.), $[\alpha]_D^{25} = +354°$ (1.03% in dimethylformamide).

EXAMPLE 18

5-Methyl-6-[4-(4-oxo-1,4-dihydropyridin-1-yl)phenyl]-4,5-dihydro-3(2H)-pyridazinone i) A solution of 2-chloropropionyl chloride (49 ml) in dichloromethane (50 ml) was added to a mixture of anhydrous aluminium trichloride (55.5 g) in dichloromethane (120 ml). The mixture was stirred for 10 minutes at room temperature and then a solution of fluorobenzene (39.5 ml) in dichloromethane (30 ml) was added dropwise. The resulting mixture was stirred for one hour, allowed to stand for 16 hours and then poured on to an icehydrochloric acid mixture. The two phase mixture was vigorously stirred at room temperature for 1½ hours, separated and the aqueous layer washed with dichloromethane (2×50 ml). The combined organic extracts were then washed with aqueous sodium hydroxide (3N, 2×100 ml), water (1×100 ml) and brine (1×100 ml), dried (MgSO₄) and evaporated under reduced pressure to afford 2-chloro-1-(4-fluorophenyl)-1-propanone, 71.3 g.

ii) Sodium hydride (50% oil dispersion, 3.5 g) was added with caution to a cooled solution of diethyl malonate (11.85 ml) in dimethylformamide (10 ml). The reaction mixture was stirred at room temperature for 30 minutes before a solution of 2-chloro-1-(4-fluorophenyl)-1-propanone (12.13 g) in dimethylformamide (50 ml) was added in small aliquots. The resulting reaction mixture was stirred for 2 hours at room temperature and then water (35 ml) was added. The mixture was extracted with petroleum ether (b.p. 40°–60° C.) (3×50 ml) and the combined organic extracts were evaporated under reduced pressure to afford ethyl 2-ethoxycarbonyl-3-(4-fluorobenzoyl)butanoate (15.92 g).

iii) Aqueous hydrochloric acid (50%, 50 ml) was added to a solution of part of the product from ii) (10 g) in dioxan (50 ml). The resulting two phase mixture was stirred under reflux for 28 hours, cooled and extracted with dichloromethane (3×50 ml). The combined organic extracts were washed with aqueous sodium hydroxide (2N, 1×100 ml, 2×50 ml) and the combined basic washings were acidified with concentrated hydrochloric acid to pH 1. The acidified aqueous mixture, containing a precipitated oil, was extracted with dichloromethane (3×50 ml). The dichloromethane extracts were combined, washed with water, dried (MgSO₄) and evaporated to dryness yielding an oil (4.87 g) which on trituration with cyclohexane afforded 3-(4-fluorobenzoyl)butanoic acid as a solid, m.p. 75°–78° C.

iv) A solution of 3-(4-fluorobenzoyl)butanoic acid (8 g), 4-hydroxypridine (8 g) and sodium hydroxide (4.6 g) in water (80 ml) was heated in an autoclave at 140° C. for 20 hours. The reaction mixture was cooled and on acidification to pH3 with dilute hydrochloric acid afforded as a white crystalline precipitate 3-[4-(4-oxo-1,4-dihydropyridin-1-yl)benzoyl]butanoic acid, 9.45 g, m.p. 250°–252° C.

v) Hydrazine hydrate (1.8 g) was added to a suspension of 3-[4-(4-oxo-1,4-dihydropyridin-1-yl)benzoyl]-butanoic acid (5 g) in water (60 ml). The resulting solution was stirred under reflux for 2 hours and cooled to afford the title compound as a pale yellow solid, 4.45 g, m.p. 255°–258° C.

EXAMPLE 19

5-Methyl-6-[4-(4-oxo-1,4-dihydropyridin-1-yl)phenyl]-4,5-dihydro-3(2H)-pyridazinone A mixture of 6-(4-aminophenyl)-5-methyl-4,5-dihydro-3(2H)-pyridazinone (101 mg), 1,5-bis(dimethylamino)-1,4-pentadien-3-one (84 mg) and hydrochloric acid (1N, 0.5 ml) in water (1.5 ml) was stirred at room temperature for 4 hours. More hydrochloric acid (1N, 0.5 ml) was added and the reaction mixture was stirred at room temperature for 18 hours and then under reflux for 4 hours to afford a quantity of red insoluble material. The hot aqueous solvent was decanted off from the insoluble material, was allowed to cool and was seeded to afford the title compound, 41 mg, m.p. 245°–249° C.

EXAMPLE 20

A pharmaceutical composition for parenteral administration is prepared by dissolving the title compound of Example 1 (0.025 g) in water (100 ml) with heating. The solution is cooled and is then sterilised by filtration through a 0.22 micron membrane filter and sealed in sterile containers suitable for injections Ph. Eur.

Compositions containing the compound of Example 1 (0.05 g) in water (100 ml) are prepared in analogous manner.

EXAMPLE 21

Pharmaceutical compositions for oral administration are prepared by combining the following:

|  | % w/w | | |
| --- | --- | --- | --- |
| 5-methyl-6-[4-(4-oxo-1,4-dihydro-pyridin-1-yl)phenyl]-4,5-dihydro-3(2H)-pyridazinone | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

What is claimed is:

1. A compound of the formula (1):

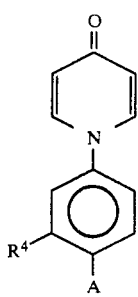

or a pharmaceutically acceptable salt thereof, wherein:
A is a group of sub-formula (a) or (b):

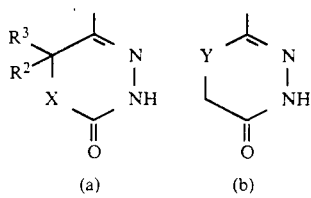

X is sulphur;
R² is hydrogen or methyl;
Y is sulphur; and
R³ and R⁴ are each hydrogen or R³ and R⁴ together form a methylene group.

2. The compound according to claim 1 wherein:
A is a group of sub-formula (a):

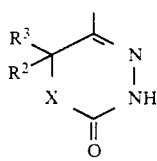

X is sulphur;
R² is hydrogen or methyl; and
R³ and R⁴ are each hydrogen.

3. The compound according to claim 2 which is 5-[4-oxo-1,4-dihydropyridin-1-yl)phenyl]-6-methyl-3H,6H-1,3,4-thiadiazin-2-one or a pharmaceutically acceptable salt thereof.

4. The compound according to claim 1 wherein:
A is a group of sub-formula (a):

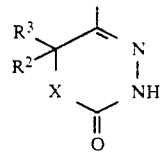

X is sulphur;
R² is hydrogen; and
R³ and R⁴ together form a methylene group.

5. The compound according to claim 4 which is:
7-(4-oxo-1,4-dihydropyridin-1-yl)-9a-methyl-9,9a-dihydroindeno[1,2-e][1,3,4]thiadiazin-2(3H)-one;
or
7-(4-oxo-1,4-dihydropyridin-1-yl)-9,9a-dihydroindeno[1,2-e][1,3,4]thiadiazin-2(3H)-one;
or a pharmaceutically acceptable salt thereof.

6. The compound according to claim 1 wherein:
A is a group of sub-formula(b):

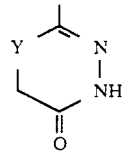

Y is sulphur;
R³ and R⁴ are each hydrogen.

7. The compound according to claim 6 which is 2-[4-(4-oxo-1,4-dihydropyridin-1-yl)phenyl]-4H,6H-1,3,4-thiadiazin-5-one or a pharmaceutically acceptable salt thereof.

8. A pharmaceutical composition which comprises a compound according to claim 1 and a pharmaceutically acceptable carrier.

9. A pharmaceutical composition according to claim 8 in unit dose form adapted for oral administration.

10. A method for stimulating cardiac activity in a host in need thereof by administration of a non-toxic but effective amount of a compound according to claim 1.

11. A method for effecting bronchodilatation in a host in need thereof by administration of a non-toxic but effective amount of a compound according to claim 1.

12. A method for effecting phosphodiesterase (type III) inhibition in a host in need thereof by administration of a non-toxic but effective amount of a compound according to claim 1.

13. A method for treating congestive heart failure in a host in need thereof by administration of a non-toxic but effective amount of a compound according to claim 1.

* * * * *